US012746155B2

(12) United States Patent
Mehta-Hurt et al.

(10) Patent No.: US 12,746,155 B2
(45) Date of Patent: Sep. 29, 2026

(54) CORNEAL LENTICULAR FORMATION USING A FEMTOSECOND LASER FOR HYPEROPIA AND MIXED ASTIGMATISM CORRECTION

(71) Applicant: AMO Development, LLC, Irvine (CA)

(72) Inventors: Deepali Mehta-Hurt, Hayward, CA (US); Cynthia Villanueva, San Jose, CA (US); Andrew Voorhees, Sunnyvale, CA (US); Athiyya Shaheen Umar Malick, Mountain House, CA (US); Wenzhi Gao, Union City, CA (US); Paul Gray, San Jose, CA (US); Li Chen, San Jose, CA (US); James Hill, Durango, CO (US); Hong Fu, Pleasanton, CA (US)

(73) Assignee: AMO Development, LLC, Irvine, CA (US)

( * ) Notice: Subject to any disclaimer, the term of this patent is extended or adjusted under 35 U.S.C. 154(b) by 139 days.

(21) Appl. No.: 18/927,801

(22) Filed: Oct. 25, 2024

(65) Prior Publication Data

US 2026/0115046 A1 Apr. 30, 2026

(51) Int. Cl.

| | |
|---|---|
| ***A61F 9/008*** | (2006.01) |
| ***A61B 17/00*** | (2006.01) |
| ***A61B 18/00*** | (2006.01) |
| ***A61B 18/20*** | (2006.01) |

(52) U.S. Cl.

CPC .................... *A61F 9/00827* (2013.01); *A61B 2017/00154* (2013.01); *A61B 2018/00601* (2013.01);

(Continued)

(58) Field of Classification Search

CPC ........ A61F 9/00827; A61F 2009/00872; A61F 2009/00878; A61F 2009/00897;

(Continued)

(56) References Cited

U.S. PATENT DOCUMENTS

| | | | |
|---|---|---|---|
| 8,685,006 | B2 | 4/2014 | Wiechmann et al. |
| 9,084,667 | B2 | 7/2015 | Bischoff et al. |

(Continued)

FOREIGN PATENT DOCUMENTS

| | | | |
|---|---|---|---|
| DE | 102019118315 | A1 | 1/2021 |
| DE | 102020112277 | A1 | 11/2021 |

(Continued)

OTHER PUBLICATIONS

International Search Report and Written Opinion, received for PCT Application No. PCT/IB2025/060827, mailed on Jan. 27, 2026, 17 pages.

*Primary Examiner* — Jonathan T Kuo

(57) ABSTRACT

An ophthalmic laser system and related method for performing corneal lenticule incision and extraction for treating hyperopia and mixed astigmatism of the eye are described. Various techniques are used to optimize the procedure for concave lenticule incisions. One technique employs a fast-scan-slow-sweep scanning scheme to form the lenticule incisions, where the sweep angle increment is set to ensure at least double-pass cut for the entire lenticule. Another technique allows for desired distribution of refractive powers between the top and bottom lenticule incisions. Other techniques configure the lenticule such that its edge thickness is a constant; or such that the highest point of the top lenticule incision, located near the lenticule periphery, is at a predefined depth below the anterior corneal surface; or to maximize lenticule thickness for refractive treatment while ensuring that minimum anterior depth and minimum residual bed thickness in the peripheral region of the lenticule are maintained.

20 Claims, 10 Drawing Sheets

(52) U.S. Cl.
CPC ............... *A61B 2018/00732* (2013.01); *A61B 2018/20353* (2017.05); *A61B 2018/20355* (2017.05); *A61F 2009/00872* (2013.01); *A61F 2009/00878* (2013.01); *A61F 2009/00897* (2013.01)

(58) Field of Classification Search
CPC ........... A61B 2017/00154; A61B 2018/00601; A61B 2018/00732; A61B 2018/20353; A61B 2018/20355
See application file for complete search history.

(56) References Cited

U.S. PATENT DOCUMENTS

| | | | | |
|---|---|---|---|---|
| 10,058,453 | B2 | 8/2018 | Seiler et al. | |
| 10,271,990 | B2 | 4/2019 | Sluyterman Van Langeweyde et al. | |
| 10,857,034 | B2 | 12/2020 | Rathjen | |
| 11,065,156 | B2 | 7/2021 | Malek Tabrizi et al. | |
| 11,717,442 | B2 | 8/2023 | Steinlechner et al. | |
| 11,759,360 | B2 | 9/2023 | Teuma et al. | |
| 12,005,001 | B2 * | 6/2024 | Voorhees ............ | A61F 9/00829 |
| 2014/0081249 | A1 * | 3/2014 | Bischoff ............. | A61F 9/00834 606/5 |
| 2016/0089270 | A1 | 3/2016 | Fu | |
| 2020/0046558 | A1 | 2/2020 | Fu et al. | |
| 2022/0054316 | A1 * | 2/2022 | Voorhees ............ | A61F 9/00827 |
| 2022/0125632 | A1 | 4/2022 | Steinlechner et al. | |
| 2023/0277377 | A1 | 9/2023 | Fu | |
| 2024/0307229 | A1 | 9/2024 | Gao et al. | |

FOREIGN PATENT DOCUMENTS

| | | | |
|---|---|---|---|
| DE | 102020114791 | A1 | 12/2021 |
| DE | 102022117348 | A1 | 1/2024 |

* cited by examiner

CORNEAL LENTICULAR FORMATION USING A FEMTOSECOND LASER FOR HYPEROPIA AND MIXED ASTIGMATISM CORRECTION

BACKGROUND OF THE INVENTION

Embodiments of this invention relate generally to laser-assisted ophthalmic procedures, and more particularly, to systems and methods for forming lenticule incisions in the cornea for hyperopic and mixed astigmatism correction.

Perfect vision, or emmetropia, occurs when the light seen by an individual is perfectly focused on the retina. Vision impairments such as myopia (near-sightedness), hyperopia (far-sightedness) and astigmatism can be corrected using eyeglasses or contact lenses. Alternatively, the cornea of the eye can be reshaped surgically to provide the needed optical correction. Eye surgery has become commonplace with some patients pursuing it as an elective procedure to avoid using contact lenses or glasses to correct refractive problems, and others pursuing it to correct adverse conditions such as cataracts. With recent developments in laser technology, laser surgery is becoming the technique of choice for ophthalmic procedures.

Hyperopia is a less common, but nevertheless important form of visual ametropia (imperfect vision). In the case of hyperopic ametropia, the light seen by an individual is focused at a single location behind the retina, leading to imperfect vision. Hyperopic astigmatism is another form of ametropia where light focuses at two different focal points beyond the retina, leading to further imperfect vision. Mixed astigmatism is a form of ametropia where the light is focused at two different focal points, one in front of the retina, and one behind the retina. Thus, one visual axis is myopic and the other visual axis is hyperopic.

There are two types of laser technologies used for refractive correction for vision impairments. The first type of laser technology relies on an excimer laser for refractive correction. An excimer can be used in two ways: 1) LASIK (Laser-Assisted In Situ Keratomileusis) or 2) PRK (Photorefractive keratectomy). In LASIK, a flap in the cornea is created and lifted, an excimer laser is used to remove some corneal material by ablation to correct the visual impairment, and the flap is reseated onto the cornea. Alternatively, in PRK, a flapless procedure, the corneal epithelium is removed from the eye, and a refractive correction is imparted onto the cornea by ablation via an excimer laser. Afterwards, the epithelium regrows back onto the cornea.

The second type of laser technology relies on a femtosecond laser to treat refractive error. A femtosecond laser is used to create a lenticule within the cornea, which is subsequently extracted from the cornea via an entry incision. In a corneal lenticule extraction procedure, instead of ablating corneal tissue with an excimer laser following the creation of a corneal flap, the technique involves tissue removal with two or more femtosecond laser incisions that intersect to create a lenticule for extraction. The extraction of the lenticule changes the shape of the cornea and its optical power to accomplish vision correction. Lenticule extractions can be performed either with or without the creation of a corneal flap. With the flapless procedure, a refractive lenticule is created in the intact portion of the anterior cornea and removed through a small incision. Methods for corneal lenticule extraction using a fast-scan-slow-sweep scanning scheme of a surgical ophthalmic laser system are described in U.S. Pat. Appl. Pub. No. 20160089270, entitled "Systems And Methods For Lenticular Laser Incision," published Mar. 31, 2016.

Using corneal lenticule extraction to correct hyperopia has been proposed. For example, FIGS. 12 and 13 of the above Publication show exemplary bi-concave lenticule profiles for hyperopic treatment. U.S. Pat. Appl. Pub. No. 2022/0054316, entitled "Corneal Lenticular Incisions with Transition Zones in Laser-Assisted Ophthalmic Procedures," published Feb. 24, 2022, also shows an exemplary bi-concave lenticule profile for hyperopic treatment (FIG. 14).

SUMMARY OF THE INVENTION

Embodiments of the present invention provide a method and related apparatus for corneal lenticule extraction useful for creating corneal lenticules for hyperopic or mixed astigmatic treatment, which are optimized for ease of extraction and visual recovery and outcome.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides a method implemented in an ophthalmic surgical laser system for forming a lenticule in a cornea of a patient's eye to treat hyperopia or mixed astigmatism, the method including: by a laser source, generating a pulsed laser beam comprising a plurality of laser pulses; by a high frequency scanner, scanning the pulsed laser beam back and forth at a predefined frequency to form a laser beam scanline, the scanline being a straight line having a defined length; by a scanline rotator, rotating a direction of the scanline around an optical axis of the laser beam; by a scanning system including an XY-scanner and a Z-scanner, delivering the scanline to the cornea and moving the scanline within the cornea in a depth direction along the optical axis of the laser beam and in two lateral directions perpendicular to the optical axis; and by a controller, controlling the laser source, the high frequency scanner, the scanline rotator, and the scanning system to successively form a first plurality of scanline sweeps which collectively form a first lenticule incision of the lenticule in the cornea, wherein each sweep is formed by placing the scanline perpendicular to a meridian of the first lenticule incision and moving the scanline along the meridian from one edge of the lenticule incision to an opposite edge of the lenticule incision, wherein a sweep angle increment between the meridians of adjacent sweeps is equal to or smaller than a value $\theta_0=\sin^{-1}(L/D)$, wherein L is the length of the scanline and D is a diameter of the lenticule incision.

In some embodiments, the method further includes, by the controller, receiving a user input specifying the diameter D of the first lenticule incision, and calculating the value $\theta_0$ based on the diameter D and the scanline length L.

In some embodiments, the method further includes, by the controller, controlling the laser source, the high frequency scanner, the scanline rotator, and the scanning system to successively form a second plurality of scanline sweeps which collectively form a second lenticule incision of the lenticule in the cornea, wherein each of the second plurality of scanline sweeps is formed by placing the scanline perpendicular to a meridian of the second lenticule incision and moving the scanline along the meridian from one edge of the second lenticule incision to an opposite edge of the second lenticule incision, wherein a sweep angle increment between the meridians of adjacent sweeps is equal to or smaller than the value $\theta_0$. In some embodiments, the meridians of the first plurality of sweeps forming the first lenticule incision and the meridians of the second plurality of sweeps forming the second lenticule incision are offset from each other by one half of the sweep angle increment.

In some embodiments, the lenticule is configured to treat mixed astigmatism of the eye, and wherein the meridian of one of the sweeps is aligned with an astigmatism axis of the eye.

In another aspect, the present invention provides an ophthalmic surgical laser system for forming a lenticule in a cornea of a patient's eye to treat hyperopia or mixed astigmatism, which includes: a laser source configured to generate a pulsed laser beam comprising a plurality of laser pulses; a high frequency scanner configured to scan the pulsed laser beam back and forth at a predefined frequency to form a laser beam scanline, the scanline being a straight line having a defined length; a scanline rotator configured to rotate a direction of the scanline around an optical axis of the laser beam; a scanning system including an XY-scanner and a Z-scanner, configured to deliver the scanline to the cornea and move the scanline within the cornea in a depth direction along the optical axis of the laser beam and in two lateral directions perpendicular to the optical axis; and a controller configured to control the laser source, the high frequency scanner, the scanline rotator, and the scanning system to successively form a first plurality of scanline sweeps which collectively form a first lenticule incision of the lenticule in the cornea, including forming each sweep by placing the scanline perpendicular to a meridian of the first lenticule incision and moving the scanline along the meridian from one edge of the lenticule incision to an opposite edge of the lenticule incision, wherein a sweep angle increment between the meridians of adjacent sweeps is equal to or smaller than a value $\theta_0=\sin^{-1}$ (L/D), wherein L is the length of the scanline and D is a diameter of the lenticule incision.

In some embodiments, the controller is further configured to receive a user input specifying the diameter D of the first lenticule incision, and to calculate the value $\theta_0$ based on the diameter D and the scanline length L.

In some embodiments, the controller is further configured to control the laser source, the high frequency scanner, the scanline rotator, and the scanning system to successively form a second plurality of scanline sweeps which collectively form a second lenticule incision of the lenticule in the cornea, including forming each of the second plurality of scanline sweeps by placing the scanline perpendicular to a meridian of the second lenticule incision and moving the scanline along the meridian from one edge of the second lenticule incision to an opposite edge of the second lenticule incision, wherein a sweep angle increment between the meridians of adjacent sweeps is equal to or smaller than the value $\theta_0$. In some embodiments, the meridians of the first plurality of sweeps forming the first lenticule incision and the meridians of the second plurality of sweeps forming the second lenticule incision are offset from each other by one half of the sweep angle increment.

In some embodiments, the lenticule is configured to treat mixed astigmatism of the eye, and wherein the meridian of one of the sweeps is aligned with an astigmatism axis of the eye.

In another aspect, the present invention provides a method implemented in an ophthalmic surgical laser system for forming a lenticule in a cornea of a patient's eye to treat hyperopia or mixed astigmatism, the method including: operating the ophthalmic surgical laser system to generate a pulsed laser beam; and scanning a focus of the laser beam in the cornea to form a top lenticule incision and a bottom lenticule incision in the cornea, wherein the top lenticule incision has a concave shape that provides a first refractive power, the bottom lenticule incision has a concave shape that provides a second refractive power higher than the first refractive power, and wherein a combined refractive power of the top and bottom lenticule incisions is equal to a defined total refractive power.

In some embodiments, the method further includes, before scanning a focus of the laser beam in the cornea to form the top and bottom lenticule incisions: receiving an input that defines total lower order refractive powers, higher order refractive powers, and a refractive power distribution ratio between the top and bottom lenticule incisions; calculating lower order refractive powers of the top and bottom lenticule incisions based on the total lower order refractive powers and the refractive power distribution ratio; and adding the higher order refractive powers to the bottom lenticule incision.

In another aspect, the present invention provides a method implemented in an ophthalmic surgical laser system for forming a lenticule in a cornea of a patient's eye to treat hyperopia or mixed astigmatism, the method including: operating the ophthalmic surgical laser system to generate a pulsed laser beam; and scanning a focus of the laser beam in the cornea to form a top lenticule incision, a bottom lenticule incision, and a ring cut in the cornea, wherein the ring cut extends along an entire periphery of the lenticule and intersect both the top and the bottom lenticule incisions to form an isolated volume of the lenticule, wherein at least one of the top and bottom lenticule incisions is a concave shape along at least one meridian and has different curvatures along two different meridians, and wherein an edge thickness of the lenticule, define as a vertical distance between an intersection of the ring cut with the top lenticule incision and an intersection of the ring cut with the bottom lenticule incision, is a constant value around an entire circumference of the lenticule.

In some embodiments, along at least some meridians, the top lenticule incision curves upwardly and then bends downwardly as it extends toward an edge of the lenticule, and the bottom lenticule incision curves downwardly and then bends upwardly as it extends toward the edge of the lenticule.

In some embodiments, the method further includes, before scanning a focus of the laser beam in the cornea: receiving one or more refractive powers and a lenticule diameter as input from a user; receiving the constant value of the edge thickness as an input from the user; and calculating shapes of the top and bottom lenticule incisions based at least in part on the one or more refractive powers, the lenticule diameter, and the constant value of the edge thickness.

In another aspect, the present invention provides a method implemented in an ophthalmic surgical laser system for forming a lenticule in a cornea of a patient's eye to treat hyperopia or mixed astigmatism, the method including: calculating a shape of a top lenticule incision of the lenticule based on a refractive power and a diameter of the top lenticule incision, the shape being a concave shape along at least some meridians, with a highest point located near a periphery of the top lenticule incision; calculating a depth of the top lenticule incision within the cornea by placing the highest point at a predefined depth below an anterior corneal surface; calculating a shape and a depth of a bottom lenticule incision of the lenticule based on a refractive power and a diameter of the bottom lenticule incision; operating the ophthalmic surgical laser system to generate a pulsed laser beam; and scanning a focus of the laser beam in the cornea to form the top lenticule incision and the bottom lenticule incision according to the calculated shapes and depths.

In some embodiments, the method further includes, before calculating a depth of the top lenticule incision, receiving the predefined depth as an input from a user.

In another aspect, the present invention provides a method implemented in an ophthalmic surgical laser system for forming a lenticule in a cornea of a patient's eye to treat hyperopia or mixed astigmatism, the method including: determining a corneal thickness in an outer area of the cornea near an edge of the lenticule; calculating a maximum lenticule thickness by subtracting a minimum anterior depth and a minimum residual bed thickness from the corneal thickness; calculating shapes of a top lenticule incision and a bottom lenticule incision, wherein along at least one meridian, both the top lenticule incision and the bottom lenticule incision have a concave shape, and wherein a vertical distance between a highest point of the top lenticule incision and a lowest point of the bottom lenticule incision is smaller than or equal to the maximum lenticule thickness; operating the ophthalmic surgical laser system to generate a pulsed laser beam; and scanning a focus of the laser beam in the cornea to form the top lenticule incision and the bottom lenticule incision according to the calculated shapes.

In some embodiments, the minimum anterior depth is from 90 to 150 μm and the minimum residual bed thickness is from 200 to 300 μm.

In another aspect, the present invention provides an ophthalmic surgical laser system which includes a laser delivery system for delivering a pulsed laser beam to a target in a subject's eye, an XY-scan device to deflect the pulsed laser beam, a Z-scan device to modify a depth of a focus of the pulsed laser beam, and a controller configured to control the XY-scan device and the Z-scan device to form a top lenticular incision and a bottom lenticular incision of a lenticule in a cornea of the subject's eye, where the controller is programmed to perform the above described methods.

It is to be understood that both the foregoing general description and the following detailed description are exemplary and explanatory and are intended to provide further explanation of the invention as claimed.

DETAILED DESCRIPTION OF THE INVENTION

As mentioned earlier, femtosecond laser systems have been used to perform corneal lenticule extraction to treat myopia and hyperopia. Embodiments of the present invention extend the application of corneal lenticule extraction to treating different forms of hyperopia such as hyperopic astigmatism as well as mixed astigmatism. Below, the femtosecond laser system and corneal lenticule formation are described first, before focusing on hyperopia and mixed astigmatism treatment.

Figure 1:
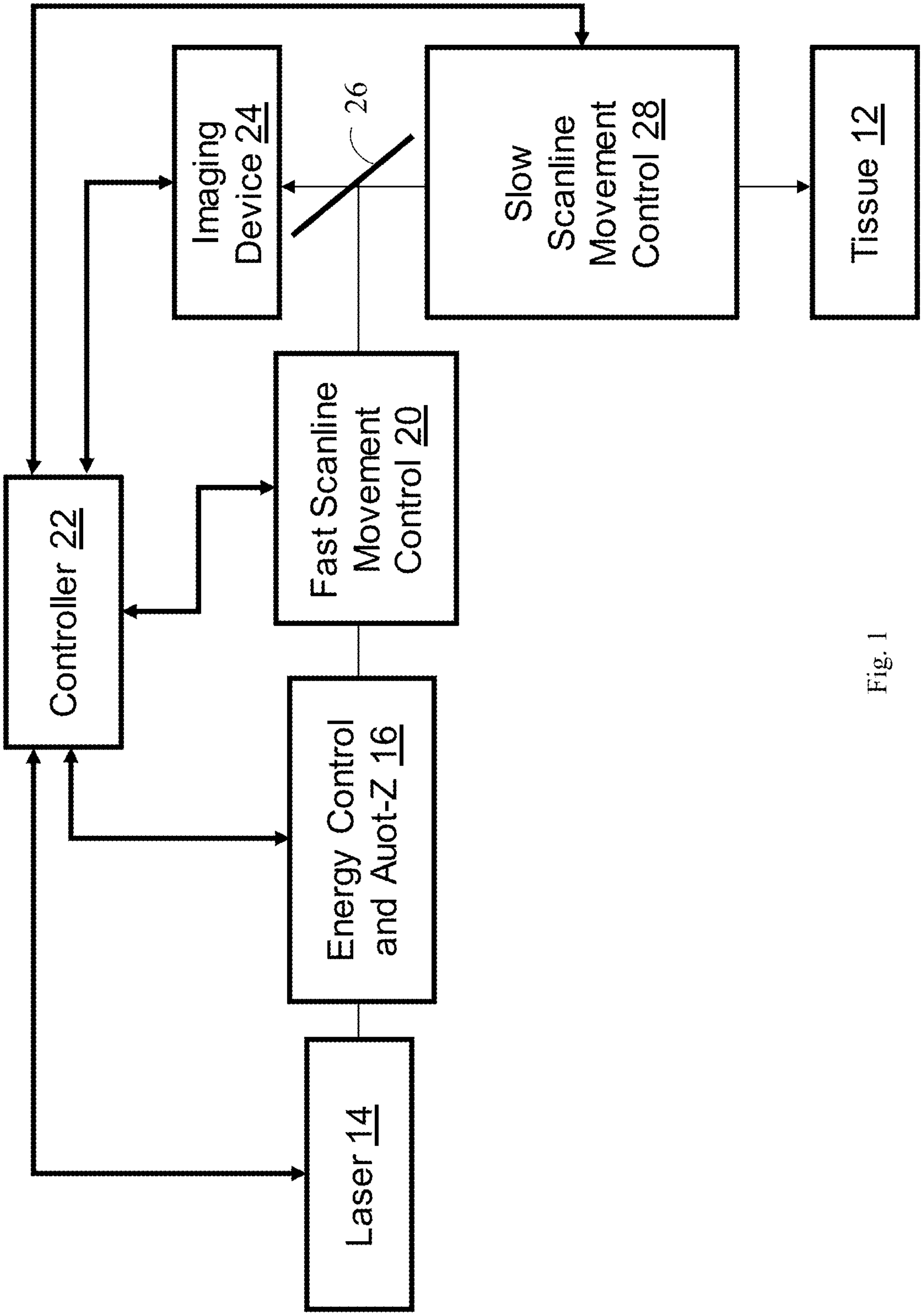
FIG. 1 is a perspective view of a surgical ophthalmic laser system which may be used to perform a lenticule incision method according to an embodiment of the present invention.

Referring to the drawings, FIG. 1 shows a system 10 for making an incision in a tissue 12 of a patient's eye. The system 10 includes, but is not limited to, a laser 14 capable of generating a pulsed laser beam, an energy control module 16 for varying the pulse energy of the pulsed laser beam, a fast scanline movement control module 20 for generating a fast scanline of the pulsed laser beam (described in more detail later), a controller 22, and a slow scanline movement control module 28 for moving the laser scanline and delivering it to the tissue 12. The controller 22, such as a processor operating suitable control software, is operatively coupled with the fast scanline movement control module 20, the slow scanline movement control module 28, and the energy control module 16 to direct the scanline of the pulsed laser beam along a scan pattern on or in the tissue 12. In this embodiment, the system 10 further includes a beam splitter 26 and an imaging device 24 coupled to the controller 22 for a feedback control mechanism (not shown) of the pulsed laser beam. Other feedback methods may also be used. In an embodiment, the pattern of pulses may be summarized in machine readable data of tangible storage media in the form of a treatment table. The treatment table may be adjusted according to feedback input into the controller 22 from an automated image analysis system in response to feedback data provided from a monitoring system feedback system (not shown).

Laser 14 may comprise a femtosecond laser capable of providing pulsed laser beams, which may be used in optical procedures, such as localized photodisruption (e.g., laser induced optical breakdown). Localized photodisruptions can be placed at or below the surface of the tissue or other material to produce high-precision material processing. For example, a micro-optics scanning system may be used to scan the pulsed laser beam to produce an incision in the material, create a flap of the material, create a pocket within the material, form removable structures of the material, and the like. The term "scan" or "scanning" refers to the movement of the focal point of the pulsed laser beam along a desired path or in a desired pattern.

In other embodiments, the laser 14 may comprise a laser source configured to deliver an ultraviolet laser beam comprising a plurality of ultraviolet laser pulses capable of photodecomposing one or more intraocular targets within the eye.

Although the laser system 10 may be used to photoalter a variety of materials (e.g., organic, inorganic, or a combination thereof), the laser system 10 is suitable for ophthalmic applications in some embodiments. In these cases, the focusing optics direct the pulsed laser beam toward an eye (for example, onto or into a cornea) for plasma mediated (for example, non-UV) photoablation of superficial tissue, or into the stroma of the cornea for intrastromal photodisruption of tissue. In these embodiments, the surgical laser system 10 may also include a lens to change the shape (for example, flatten or curve) of the cornea prior to scanning the pulsed laser beam toward the eye.

Figure 2:
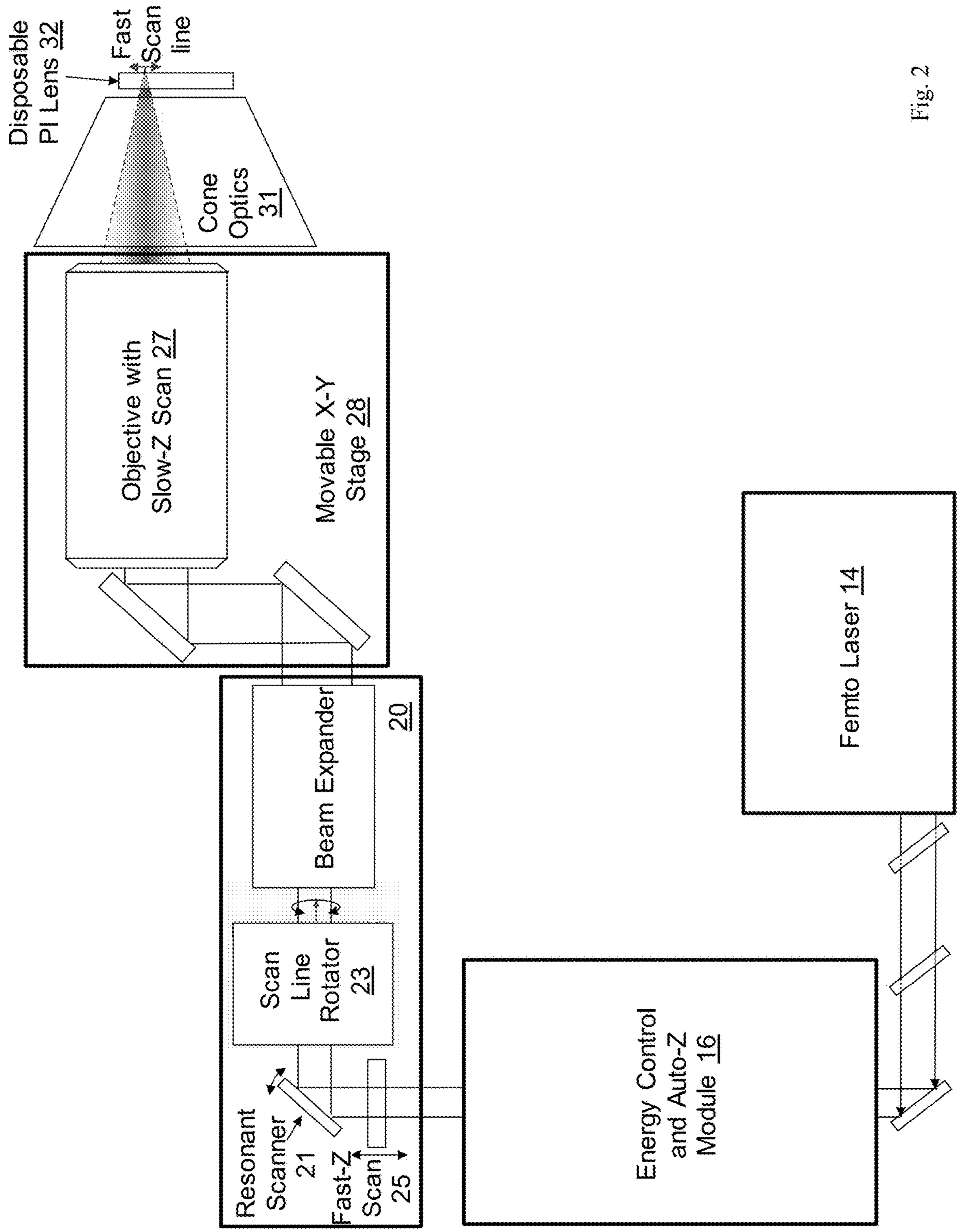
FIG. 2 is another perspective view of a surgical ophthalmic laser system which may be used to perform a lenticule incision method according to an embodiment of the present invention.

FIG. 2 shows another exemplary diagram of the laser system 10. FIG. 2 shows components of a laser delivery system including a moveable XY-scanner (or movable XY-stage) 28 of a miniaturized femtosecond laser system. In this embodiment, the system 10 uses a femtosecond oscillator, or a fiber oscillator-based low energy laser. This allows the laser to be made much smaller. The laser-tissue interaction is in the low-density-plasma mode. An exemplary set of laser parameters for such lasers include pulse energy in the 40-100 nJ range and pulse repetitive rates (or "rep rates") in the 2-40 MHz range. A fast-Z scanner 25 and a resonant scanner 21 direct the laser beam to a scanline rotator 23. When used in an ophthalmic procedure, the system 10 also includes a patient interface design that has a fixed cone nose 31 and a contact lens 32 that engages with the patient's eye. A beam splitter may be placed inside the cone 31 of the patient interface to allow the whole eye to be imaged via visualization optics. In some embodiments, the system 10 may use: optics with a 0.6 numerical aperture (NA) which would produce 1.1 μm Full Width at Half Maximum (FWHM) focus spot size; and a resonant scanner 21 that produces 0.2-1.2 mm scan line with the XY-scanner scanning the resonant scan line to a 1.0 mm field. The prism 23 (e.g., a Dove or Pechan prism, or the like) rotates the resonant scan line in any direction on the XY plane. The fast-Z scanner 25 sets the incision depth. The slow scanline movement control module employs a movable XY-stage 28 carrying an objective lens with Z-scanning capability 27, referred to as slow-Z scanner because it is slower than the fast-Z scanner 25. The movable XY-stage 28 moves the objective lens to achieve scanning of the laser scanline in the X and Y directions. The objective lens changes the depth of the laser scanline in the tissue. The energy control and auto-Z module 16 may include appropriate components to control the laser pulse energy, including attenuators, etc. It may also include an auto-Z module which employs a confocal or non-confocal imaging system to provide a depth reference. The miniaturized femtosecond laser system 10 may be a desktop system so that the patient sits upright while being under treatment. This eliminates the need of certain opto-mechanical arm mechanism(s), and greatly reduces the complexity, size, and weight of the laser system. Alternatively, the miniaturized laser system may be designed as a conventional femtosecond laser system, where the patient is treated while lying down.

Figure 3:
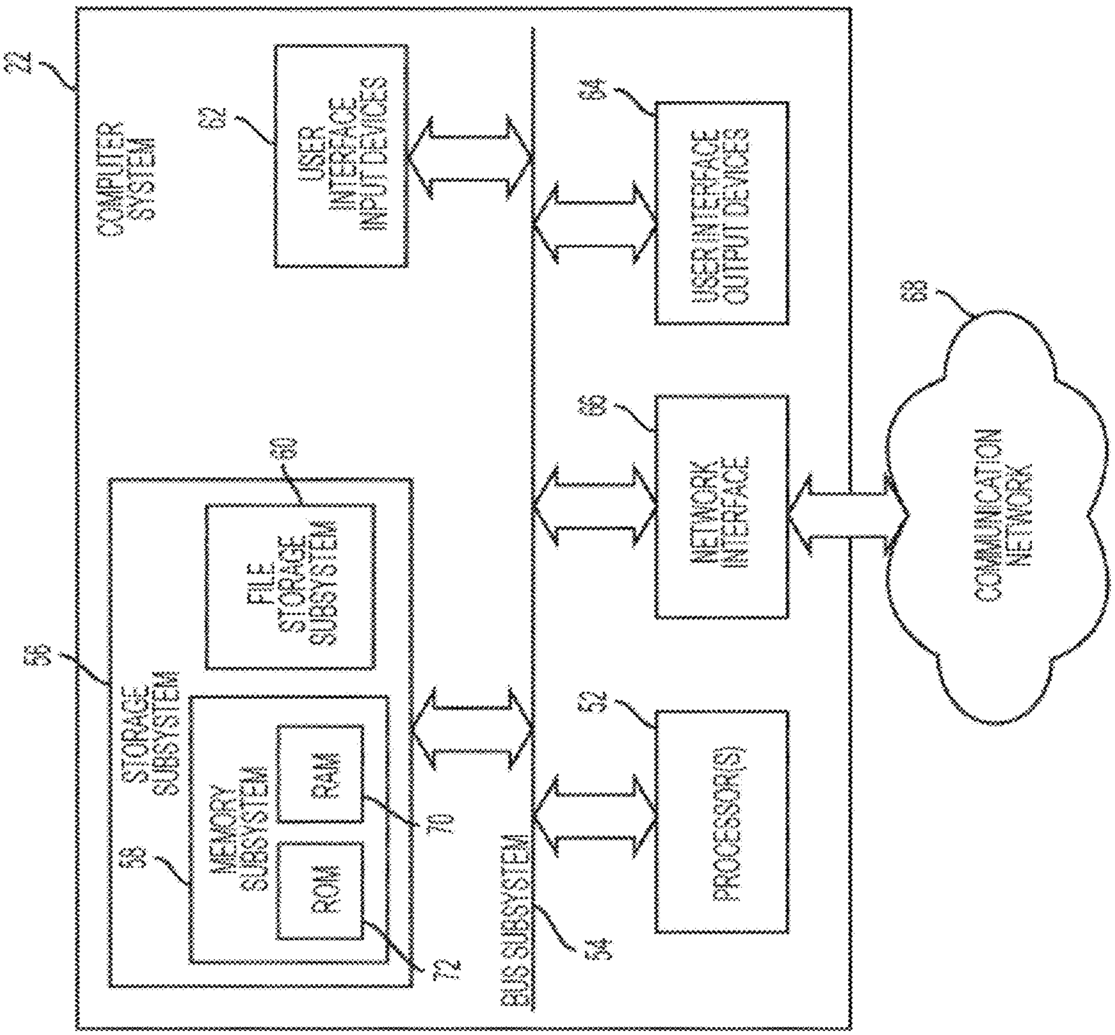
FIG. 3 is a simplified diagram of a controller of a surgical ophthalmic laser system which may be used to perform a lenticule incision method according to an embodiment of the present invention.

FIG. 3 illustrates a simplified block diagram of an exemplary controller 22 that may be used by the laser system 10 according to an embodiment of this invention to control the laser system 10 and execute at least some of the steps discussed in detail below. Controller 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices. Network interface subsystem 66 includes one or more interfaces known in the arts, such as LAN, WLAN, Bluetooth, other wire and wireless interfaces, and so on.

User interface input devices 62 may include a keyboard, pointing devices such as a mouse, trackball, touch pad, or graphics tablet, a scanner, foot pedals, a joystick, a touch screen incorporated into a display, audio input devices such as voice recognition systems, microphones, and other types of input devices. In general, the term "input device" is intended to include a variety of conventional and proprietary devices and ways to input information into controller 22. User interface output devices 64 may include a display subsystem, a printer, a fax machine, or non-visual displays such as audio output devices. The display subsystem may be a flat-panel device such as a liquid crystal display (LCD), a light emitting diode (LED) display, a touchscreen display, or the like. The display subsystem may also provide a non-visual display such as via audio output devices. In general, the term "output device" is intended to include a variety of conventional and proprietary devices and ways to output information from controller 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60. Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files. File storage subsystem 60 may include a hard disk drive along with associated removable media, a Compact Disk (CD) drive, an optical drive, DVD, solid-state memory, and/or other removable media. One or more of the drives may be located at remote locations on other connected computers at other sites coupled to controller 22. The modules implementing the functionality of the present invention may be stored by file storage subsystem 60.

Bus subsystem 54 provides a mechanism for letting the various components and subsystems of controller 22 communicate with each other as intended. The various subsystems and components of controller 22 need not be at the same physical location but may be distributed at various locations within a distributed network. Although bus subsystem 54 is shown schematically as a single bus, alternate embodiments of the bus subsystem may utilize multiple busses. Due to the ever-changing nature of computers and networks, the description of controller 22 depicted in FIG. 3 is intended only as an example for purposes of illustrating only one embodiment of the present invention. Many other configurations of controller 22, having more or fewer components than those depicted in FIG. 3, are possible.

As should be understood by those of skill in the art, additional components and subsystems may be included with laser system 10. For example, spatial and/or temporal integrators may be included to control the distribution of energy within the laser beam. Ablation effluent evacuators/filters, aspirators, and other ancillary components of the surgical laser system are known in the art, and may be included in the system. In addition, an imaging device or system may be used to guide the laser beam.

Figure 4:
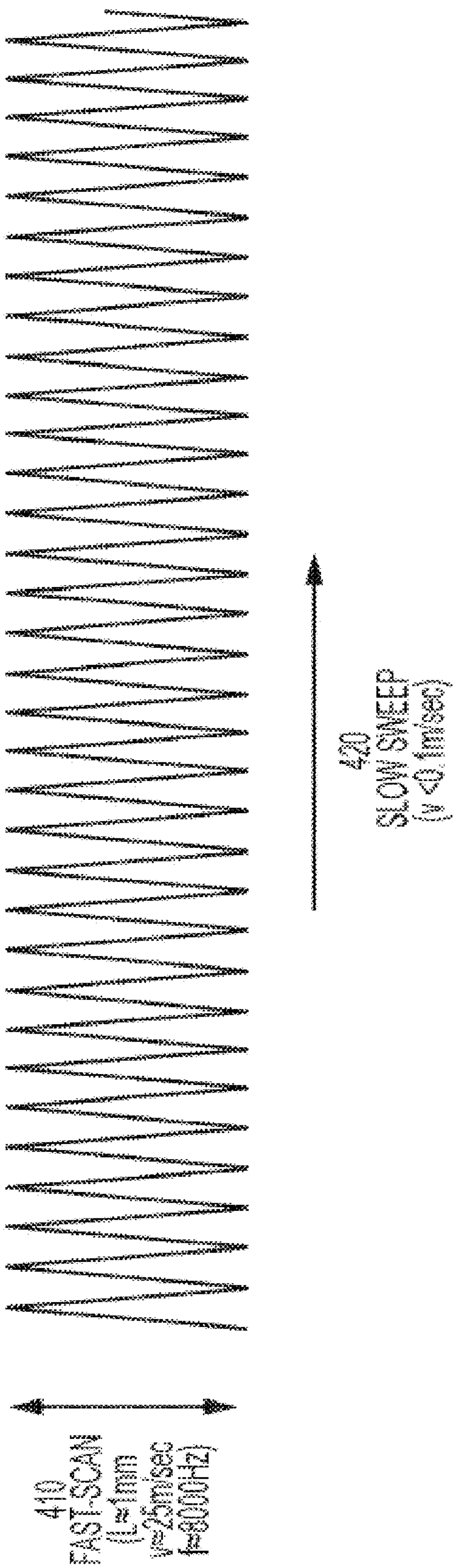
FIG. 4 illustrates an exemplary scanning of a surgical ophthalmic laser system according to an embodiment of the present invention.

In preferred embodiments, the beam scanning can be realized with a "fast-scan-slow-sweep" scanning scheme, also referred herein as a fast-scan line scheme. The scheme consists of two scanning mechanisms: first, a high frequency fast scanner is used to scan the beam back and forth to produce a short, fast scan line (e.g., a resonant scanner 21 of FIG. 2); second, the fast scan line is slowly swept by much slower X, Y, and Z scan mechanisms (e.g. the moveable X-Y stage 28 and the objective lens with slow-Z scan 27, and the fast-Z scanner 25). FIG. 4 illustrates a scanning example of a laser system 10 using an 8 kHz (e.g. between 7 kHz and 9 kHz, or more generally, between 0.5 kHz and 20 kHz) resonant scanner 21 to produce a fast scan line 410 of about 1 mm (e.g., between 0.9 mm and 1.1 mm, or more generally, between 0.2 mm and 1.2 mm) and a scan speed of about 25 m/sec, and X, Y, and Z scan mechanisms with the scan speed (sweeping speed) smaller than about 0.1 m/sec. The fast scan line 410 may be perpendicular to the optical beam propagation direction, i.e., it is always parallel to the XY plane. The trajectory of the slow sweep 420 can be any three dimensional curve drawn by the X, Y, and Z scanning devices (e.g., XY-scanner 28 and fast-Z scanner 25). An advantage of the "fast-scan-slow-sweep" scanning scheme is that it only uses small field optics (e.g., a field diameter of 1.5 mm) which can achieve high focus quality at relatively low cost. The large surgical field (e.g., a field diameter of 10 mm or greater) is achieved with the XY-scanner, which may be unlimited.

Figure 5:
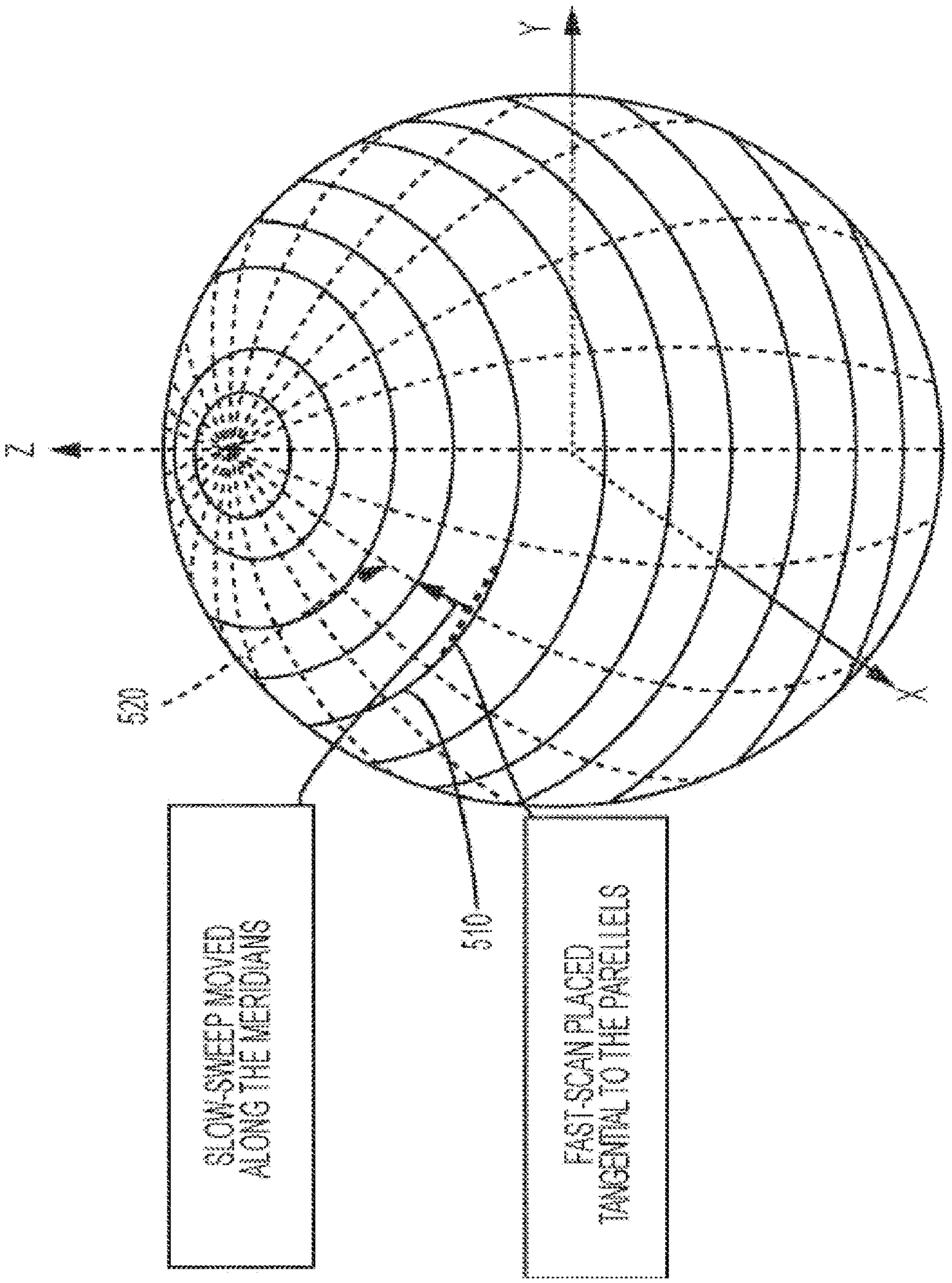
FIG. 5 illustrates an exemplary surface dissection using a fast-scan-slow-sweep scheme of a surgical ophthalmic laser system according to an embodiment of the present invention.
Figure 7:
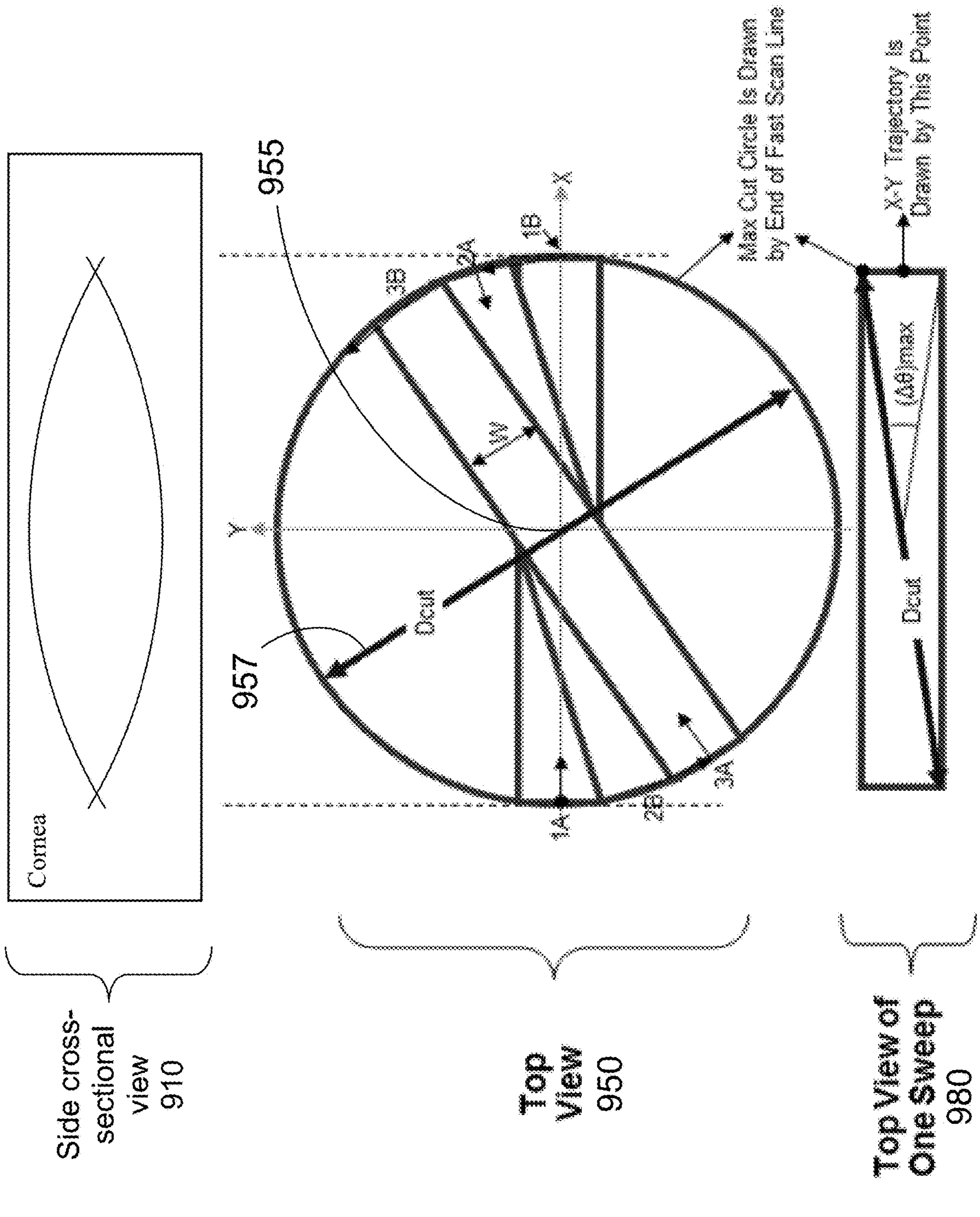
FIG. 7 illustrates an exemplary lenticular incision using a surgical ophthalmic laser system according to an embodiment of the present invention.

In a preferred embodiment shown in FIGS. 5 and 7, the laser system 10 creates a smooth lenticular cut using the "fast-scan-slow-sweep" scanning scheme under a preferred procedure. First, in a three dimensional lenticular cut, the fast scan line is preferably placed tangential to the parallels of latitude 510 on the surface of the lenticule. A parallel of latitude is the intersection of the surface with a plane perpendicular to the Z axis (which is the axis parallel to the depth direction of the eye), i.e. a circle on the surface of the lens that is perpendicular to the Z axis and has a defined distance to the apex (the highest point in the Z direction). For example, in the laser system 10 of FIG. 2, this can be realized by adjusting a prism 23 to the corresponding orientations via software, e.g., via the controller 22. Second, the slow sweep trajectory preferably moves along the meridians of longitude 520 on the surface of the lenticule. A meridian of longitude is the intersection of the surface with a plane that passes through the Z axis, i.e. a curve that passes through the apex and has a defined angular direction with respect to the Z axis. For example, in the laser system of FIG. 2, this can be done by coordinating the XY scanner 28, and the Fast-Z scanner 25 via the software, e.g., via the controller 22. The procedure starts with the scan line being parallel to the XY plane, and sweeps through the apex of the lens, following the curvature with the largest diameter (see also FIG. 7, top view). Multiple sweeps are performed at successive angular directions with respect to the Z axis, for example as realized by rotating the prism 23 between successive sweeps, to form the entire lenticule. With this preferred procedure, there are no vertical "steps" in the dissection, and vertical side cuts are eliminated. As will be analyzed herein below, the deviations between the laser focus locations and the intended spherical surface dissections are also minimized.

Figure 6:
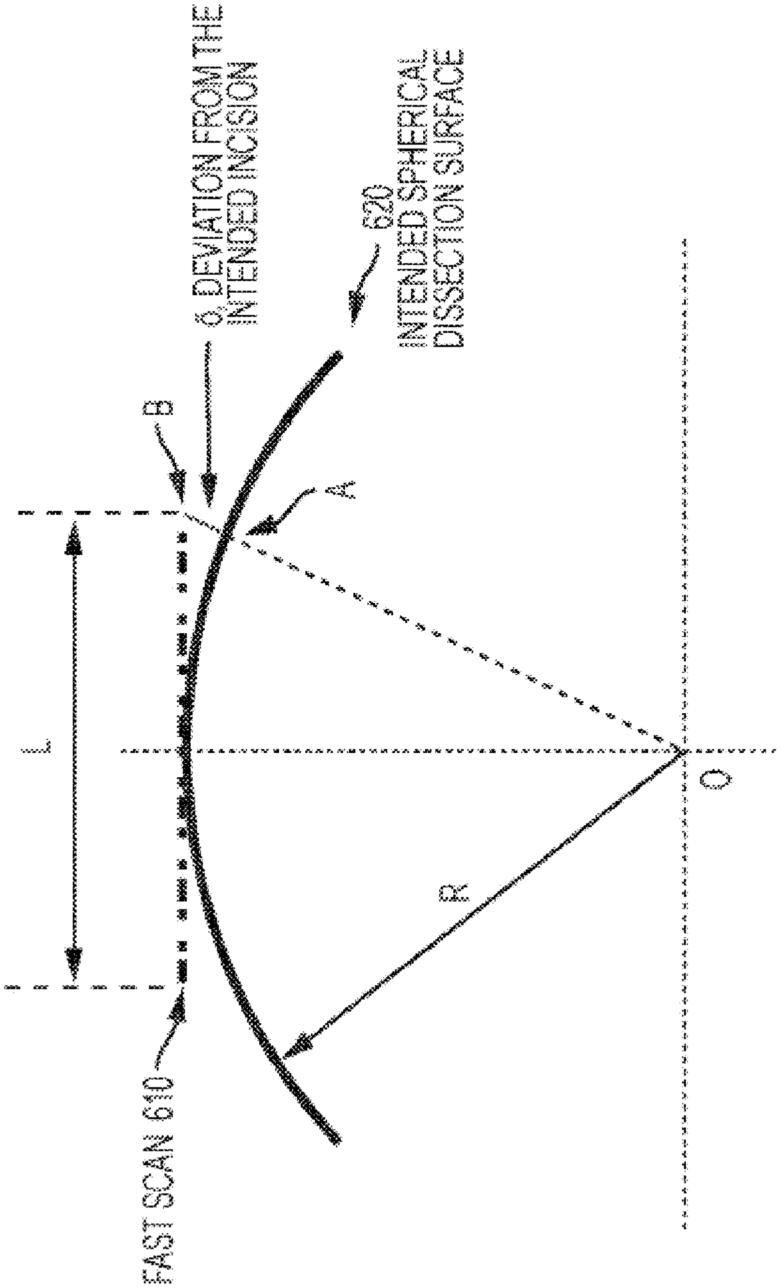
FIG. 6 illustrates a geometric relation between a fast-scan line and an intended spherical dissection surface of a surgical ophthalmic laser system according to an embodiment of the present invention.

FIG. 6 shows the geometric relation between the fast scan line 610 and the intended spherical dissection surface 620, e.g., of a lens, especially the distance deviation (δ) between the end point B of the scan line 610 and point A on the intended dissection surface 620. The maximum deviation δ is the distance between point A and point B, and is given by (Equation (1)):

$$\delta = \sqrt{R^2 + \frac{L^2}{4}} - R \approx \frac{L^2}{8R}$$

where R is greater than L. R is the radius of curvature of the surface dissection 620, and L is the length of the fast scan.

While the above maximum deviation analysis is for a spherical surface, this scanning method may also be used to create a smooth cut having a non-spherical shape, such as an ellipsoidal shape, etc. In such a case, the parallel of latitude and/or the meridian of longitude may not be circular.

In an exemplary case of myopic correction, the radius of curvature of the surface dissection may be determined by the amount of correction, ΔD, using the following equation (Equation (2)):

$$\Delta D = \frac{(n-1)}{R_1} + \frac{(n-1)}{R_2}$$

where n=1.376, which is the refractive index of cornea, and R1 and R2 (may also be referred herein as Rt and Rb) are the radii of curvature for the top surface and bottom surface of a lenticular incision, respectively. For a lenticular incision with R1=R2=R (the two dissection surface are equal for them to physically match and be in contact), we have (Equation (3)):

$$R = \frac{2(n-1)}{\Delta D}$$

FIG. 7 is a top view 950 of a lenticular incision 900 which illustrates three exemplary sweeps (1A to 1B), (2A to 2B) and (3A to 3B), with each sweep going through (i.e., going over) the lenticular incision apex 955. The incision diameter 957 (DCUT) should be equal to or greater than the to-be-extracted lenticular incision diameter. A top view 980 shows the top view of one exemplary sweep. FIG. 7 also illustrates a side cross-sectional view 910 of the lenticule in an applanated cornea, formed by a top (anterior) lenticule incision and a bottom (posterior) lenticule incision that intersect each other.

Features of the embodiments of the present invention are described below. These features are specifically aimed at creating a lenticule for treating hyperopia and/or mixed astigmatism, and are optimized for ease of lenticule extraction and visual recovery and outcome for such procedures.

In a first embodiment of the present invention, the relative angle between adjacent scanline sweeps, referred to as the sweep angle increment (θ), is set based on the lenticule diameter, to ensure double pass cut near the lenticule periphery. Note that since each sweep proceeds along a meridian of longitude of the lenticule, the sweep angle increment is the angle between the meridians of adjacent sweeps.

Figure 8:
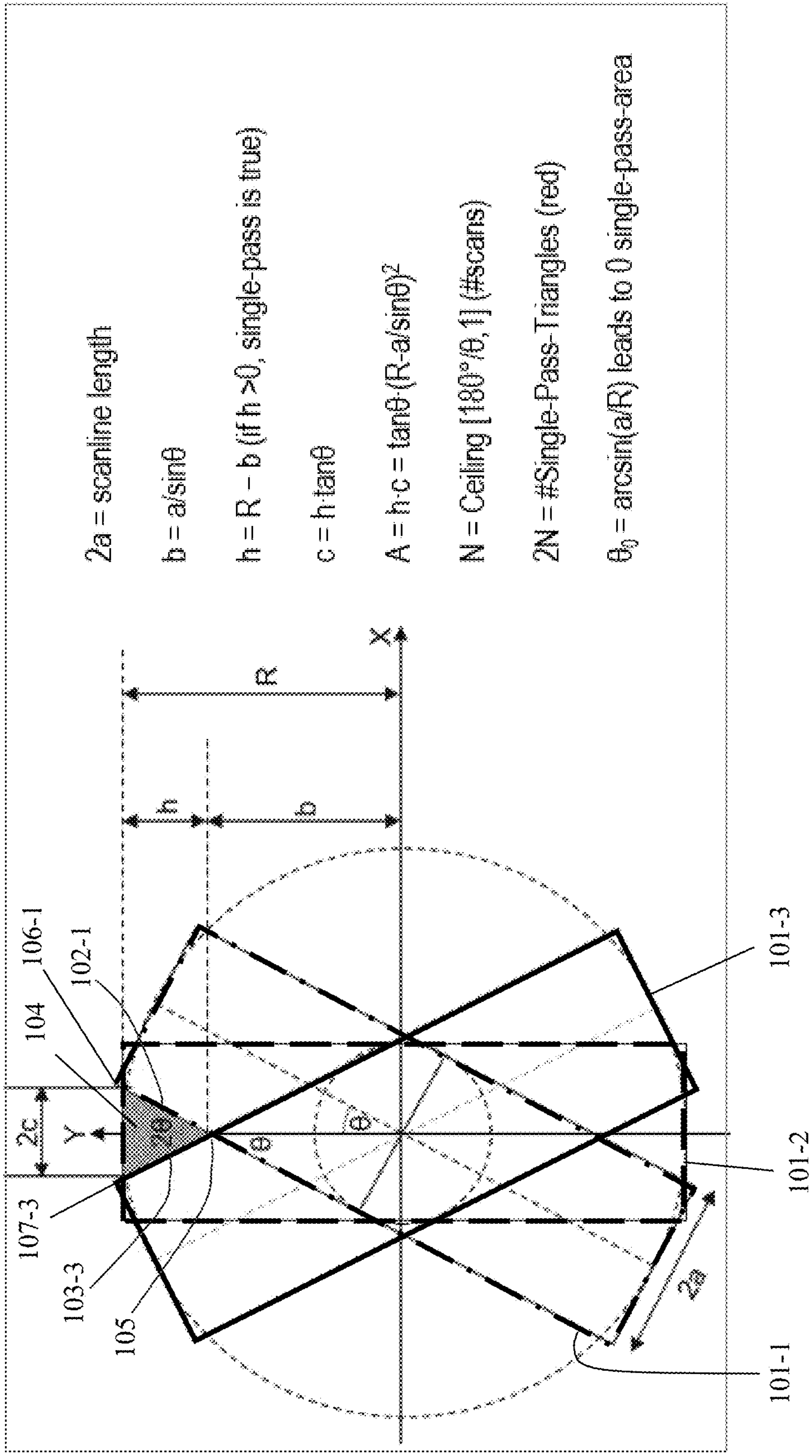
FIG. 8 schematically illustrates a method for lenticule incision using a fast-scan-slow-sweep laser scanning scheme according to an embodiment of the present invention.

FIG. 8 (top plan view) schematically illustrates the effect of the sweep angle increment parameter θ, showing that whether the lenticule incision has regions of single pass cut is affected by the value of θ selected. FIG. 8 shows the formation of either a top or a bottom lenticule incision, where three successive sweeps of the laser beam scanline are represented by three rectangles 101-1 (dot-dashed lines), 101-2 (dashed line) and 101-3 (solid lines), with the directions of successive sweeps being rotated by the angle θ in the counterclockwise direction. The triangular area 104 near the periphery of the lenticule within the second sweep 101-2, located between the leading side 102-1 of the first sweep 101-1 and the trailing side 103-3 of the third sweep 101-3, is only covered by the second sweep 101-2. Assuming a fixed scanline length 2a, the larger the lenticule diameter 2R, the larger the single-pass areas 104 for a given sweep angle increment θ. Larger single pass areas may lead to tissue stickiness and difficulty in lenticule extraction. According to a first embodiment of the present invention, the sweep angle increment θ is set based on the lenticule diameter, to ensure double pass near the lenticule periphery along the entire circumference. As illustrated in FIG. 8, the distance b from the lenticule center to the intersection 105 of the leading side 102-1 of the first sweep and the trailing side 103-3 of the third sweep is:

$$b = a/\sin\theta,$$

where a is one half of the scanline length. The difference h between R (the radius of the lenticule) and b is the height of the single-pass area 104. To eliminate the single-pass area 104, the intersection 105 should be located at the periphery of the lenticule, i.e., b=R. Therefore, the sweep angle increment $\theta_0$ that will eliminate single-pass areas is:

$$\theta_0 = \sin^{-1}(a/R) = \sin^{-1}(L/D),$$

where L=2a is the scanline length, and D=2R is the lenticule diameter. Visually, $\theta_0$ is the sweep angle increment such that the leading corner 106-1 of a current sweep (e.g. the first sweep 101-1) and the trailing corner 107-3 of the second subsequent sweep (e.g. the third sweep 101-3) coincide with each other. Any sweep angle increments equal to or smaller than $\theta_0$ will eliminate single pass areas, i.e., will ensure that any area within the entire lenticule is cut by at least two sweeps.

In practice, during the corneal lenticule extraction procedure, the controller of the laser system may be programmed to automatically calculate $\theta_0$ based on other parameters input by the user, such as lenticule diameter and scanline length, using the above equation.

It should be noted that the lenticule diameter D is the diameter of the total cutting area of the lenticule, including both the optical zone and the transition zone: D=OZ+(2*TW), where OZ is the optical zone diameter and TW is the transition zone width. In the front plan view, the optical zone is a central region of the lenticule where the curvature of the top and bottom lenticule incisions define the refractive optical properties of the lenticule for vision correction. The transition zone is a ring shaped area at the periphery of the lenticule surrounding the optical zone, where the shape of the top and bottom lenticule incisions, and a ring cut that connects the top and bottom lenticule incisions (optional, see FIGS. 9A-9C described later), do not contribute to the refractive optical properties of the lenticule but are designed for practical purposes such as the mechanical properties of the lenticule, case of lenticule extraction, etc.

For hyperopia treatment, both the optical zone and transition zone are typically larger than in a lenticule for myopia treatment. In one particular example, OZ=7.5 mm, TW=0.8 mm, which gives D=9.1 mm. If the scanline width is L=0.9 mm, then, the sweep angle increment that will eliminate single-pass areas is $\theta_0=\sin^{-1}(0.9/9.1)=5.68°$.

Preferably, the same sweep angle increment values are used for cutting the top and bottom lenticular incisions. In some embodiments, to obtain more uniform scanning patterns on the corneal interface after the lenticule is removed, it is desirable to offset the top and bottom scan patterns by one half of the sweep angle increment, e.g. $\theta_0/2=2.84°$. In some other embodiment, when forming a lenticule for treating mixed astigmatism, the first sweep starts from one of the astigmatism axes for both the top and the bottom lenticule incisions, to ensure that these special meridians are formed by a sweep that precisely align with the astigmatism axis.

As shown in FIG. 8, for a given sweep angle increment θ and scanline length 2a, the larger the lenticule radius R (when R>b), the larger the single-pass area 104. The height h of the triangular single-pass area is h=R−b and the base 2*c* of the single-pass area is 2c=2*h*tan θ. The single-pass areas are more of a concern for lenticules for treating hyperopia or mixed astigmatism, because these lenticules typically have larger diameters (e.g. typically 9.5 mm) than that of lenticules for treating myopia (e.g. typically 8.0 mm), and extend farther into the outer areas of the cornea. In the outer areas, the corneal tissue structure is different from the center areas, and the presence of single-pass areas in the outer areas creates a challenge not faced in lenticule extraction procedures for myopia treatment. The first embodiment of the present invention solves this problem by reducing the sweep angle increment to eliminate single-pass areas throughout the entire lenticule.

Figure 9A:
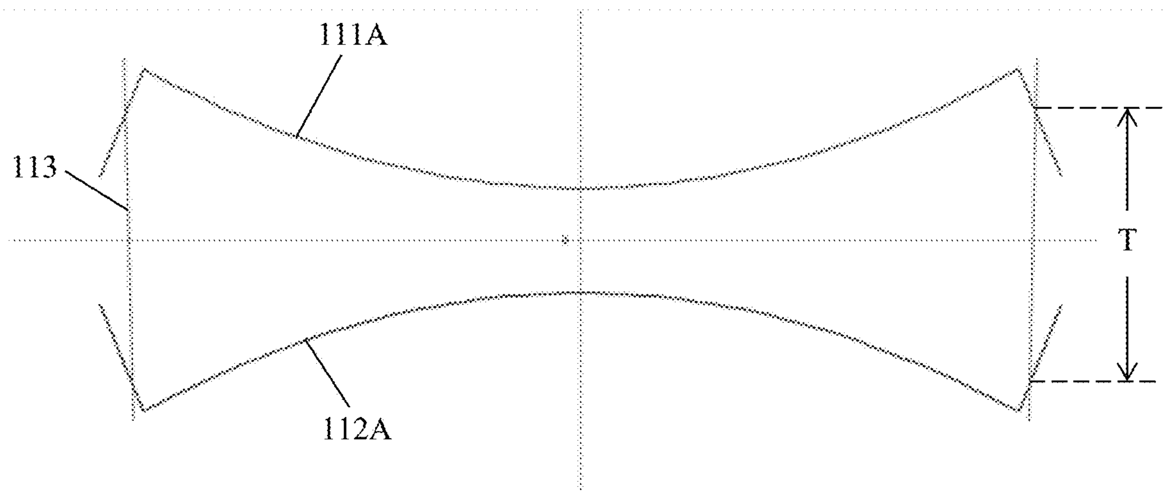
FIGS. 9A-9C schematically illustrate the depth profiles of bi-concave corneal lenticules for hyperopia correction according to embodiments of the present invention.

In a second embodiment of the present invention, the shapes of the top and bottom lenticule incisions are configured to provide them with different refractive powers. FIG. 9A (side cross-sectional view, with cornea under applanation) schematically illustrates a bi-concave lenticule for hyperopia correction, where the top lenticule incision 111A and the bottom lenticule incision 112A are both concave and have the same curvature, i.e., the same refractive power. The combined refractive power of the two incisions determines the amount of refractive correction of the lenticule. In this disclosure, the term "concave" and "convex" refer to the shape from the perspective of the lenticule.

Figure 9B:
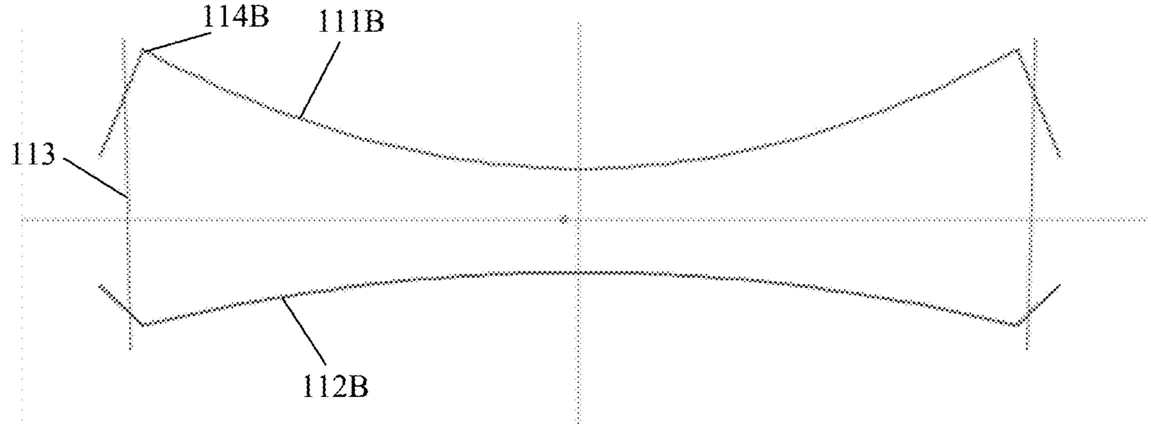

FIG. 9B (side cross-sectional view, with cornea under applanation) schematically illustrates a bi-concave lenticule for hyperopia correction according to the second embodiment, where the top lenticule incision 111B and the bottom lenticule incision 112B are both concave but have different curvatures, i.e., different refractive powers (in this example, higher power at the top lenticule incision). Again, the combined refractive power of the two incisions determines the amount of refractive correction of the lenticule. In other words, the refractive power distribution between the top and bottom lenticule incisions can be configured to be an equal distribution (FIG. 9A) or an unequal distribution (FIG. 9B).

Figure 9C:
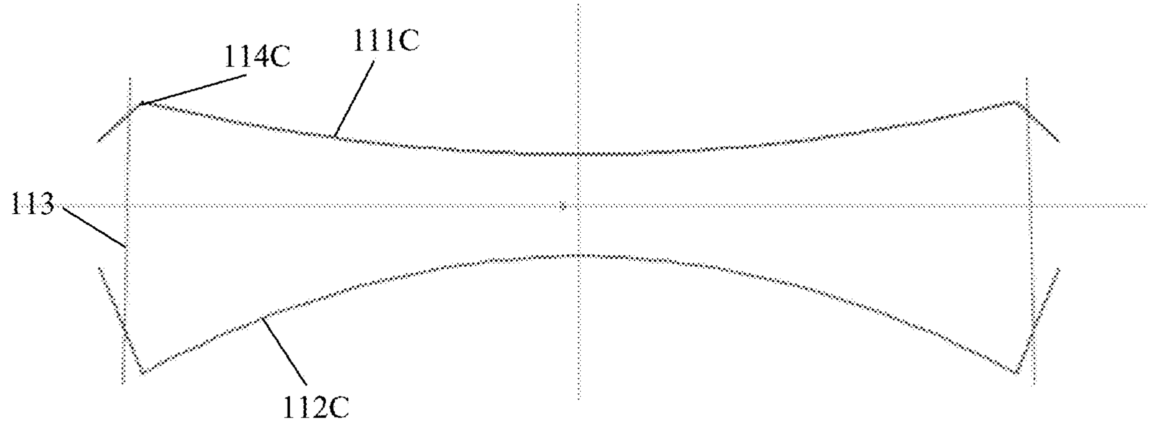

In another example shown in FIG. 9C, the refractive power distribution is configured such that the top lenticule incision 111C has less spherical refractive power, i.e. lower curvature, than the bottom lenticule incision 112C. For hyperopia correction, because the lenticule is thicker near the periphery than at the center, a larger curvature at the top lenticule incision may cause the highest point 114B (see FIG. 9B) of the top lenticule incision to come too close to the anterior corneal surface. Distributing more of the spherical refractive power to the bottom lenticule incision as in FIG. 9C will help reduce the curvature of the top lenticule incision and the height of the highest point 114C.

In another example, the refractive power distribution is configured such that the correction for all higher order aberrations (e.g., spherical aberration, coma, and trefoil) are defined only on the bottom lenticule incision. This again may help to reduce the height of the lenticule near the top edge.

In practice, the refractive powers of the top and bottom lenticule incisions may be calculated by the controller based on user inputs of the total refractive power (including lower and higher order aberration correction) and a refractive power distribution ratio between the top and bottom lenticule incisions. The controller calculates the lower order (spherical, cylindrical) refractive powers for the top and bottom lenticule incisions based on the total lower order refractive powers and the refractive power distribution ratio, before adding the higher order refractive powers to the bottom lenticule incision.

The flexibility in distribution refractive powers allows for optimizing laser-tissue interactions, because at different corneal depths the collagen fiber density is different, so the bubble dynamics (i.e., the generation of opaque gas bubbles by the laser pulses during laser-tissue interaction, and management of bubbles) can be optimized to achieve better incision quality and easier lenticule removal. Moreover, by choosing different curvatures for the top and bottom lenticule incisions, the surface matching after lenticule removal can be optimized, thereby reducing corneal folds at the interface that can lead to scattered light, and reducing halo and glare.

FIGS. 9A-9C also show a ring cut 113, which is a ring shaped incision that extends along the entire periphery of the lenticule. The ring cut 113 extends vertically or near vertically to intersect both the top lenticule incision 111A-C and the bottom lenticule incision 112A-C in the periphery region, thereby forming an isolated volume of the lenticule. In the illustrated embodiments, the top lenticule incision 111A-C bends downwardly near the periphery before it intersects the ring cut, and the bottom lenticule incision 112A-C bends upwardly near the periphery before it intersects the ring cut. It should be noted that while the illustrated embodiments show relatively sharp bends, the bends may have a rounded shape. The bending portions and the ring cut are located in the transition zone of the lenticule and do not affect the refractive correction of the lenticule. The bend is optional. It should also be noted that the shapes of the lenticule incisions in these figures are exaggerated and not to scale.

In a third embodiment of the present invention, the top and bottom lenticule incisions are configured so that the edge thickness of the lenticule is a constant around the entire circumference. As shown in FIG. 9A, the edge thickness T of the lenticule is the vertical distance between the intersection of the ring cut 113 with the top lenticule incision 111A and the intersection of the ring cut with the bottom lenticule incision 112A. The requirement for a constant edge thickness is significant for lenticules that treat astigmatism, and in particular, mixed astigmatism, because such lenticules would otherwise tend to have non-constant edge thickness due to the different curvatures along different meridians. The difference in edge thickness would be the greatest between the two meridians that are respectively parallel and perpendicular to the astigmatism axis. In this embodiment, a constant edge thickness is achieved by different amount of peripheral bending of the top and bottom lenticule incisions along different meridians. It should be noted that although the lenticule incisions are no longer spherical in shape when hyperopic astigmatism and mixed astigmatism treatments are required, the term "meridian" is still used here to refer to the angular direction of the sweeps; a meridian may be defined as the intersection of the lenticule surface and a plane that passes through the central axis of the lenticule.

In practice, the peripheral shapes of the top and bottom lenticule incisions that maintain a constant edge thickness may be calculated by the controller based on user input parameters, including the edge thickness value. Alternatively, the controller may use a pre-set edge thickness value. The controller calculates the shapes of the top and bottom lenticule incisions, including the amount of the peripheral bend, for the input combinations of other lenticule parameters to maintain the constant edge thickness as specified by the user input or the pre-set value.

The constant edge thickness helps in the preservation of corneal tissue in the patient's eye as well as recovery and corneal stability. The constant (and selectable) lenticule edge thickness at all meridian angles and for different treatment prescriptions will improve the consistency of the lenticule removal and the outcome of the procedure.

In a fourth embodiment of the present invention, the lenticule incisions are configured such that the highest points of the lenticule, which are located near the periphery of the top lenticule incision, are at a desired depth from the anterior corneal surface. This is particularly important for lenticules for hyperopia and mixed astigmatism treatments. For a lenticule for myopia treatment, the top lenticule incision is convex or plano, so the highest point of the lenticule is at the center of the top lenticule incision. Conventionally, the lenticule incisions are configured by setting the depth of the center of the top lenticule incision to a desired value, and the rest of the calculation is performed on that basis. For a lenticule for hyperopia or mixed astigmatism treatments, however, because the highest point of the lenticule is located near the periphery (e.g., point 114B in FIG. 9B), if the center of the top lenticule is set at a particular depth, the highest point may become too close to the anterior corneal surface. Moreover, the height of the highest point (relative to the top lenticule center) is dependent on the refractive power and the size of the lenticule, and also dependent on the meridian angle in a lenticule for treating hyperopia with astigmatism or mixed astigmatism, all of which make the height of the highest point difficult to control if the lenticule is configured by setting the depth of the top lenticule center.

To solve this problem, in the fourth embodiment, the lenticule incisions are configured by setting the depth of the highest point of the lenticule to a desired value. After the shapes of the top and bottom lenticule incisions are calculated based on the various lenticule parameters, the depth of the lenticule within the cornea is calculated by placing the highest point of the top lenticule incision at the desired depth below the anterior corneal surface. Preferably, the depth of the highest point of the lenticule is set at 90 μm to 150 μm from the anterior corneal surface. In practice, the depth of the highest point may be input by the user, or set at a pre-set value by the controller.

Figure 10A:
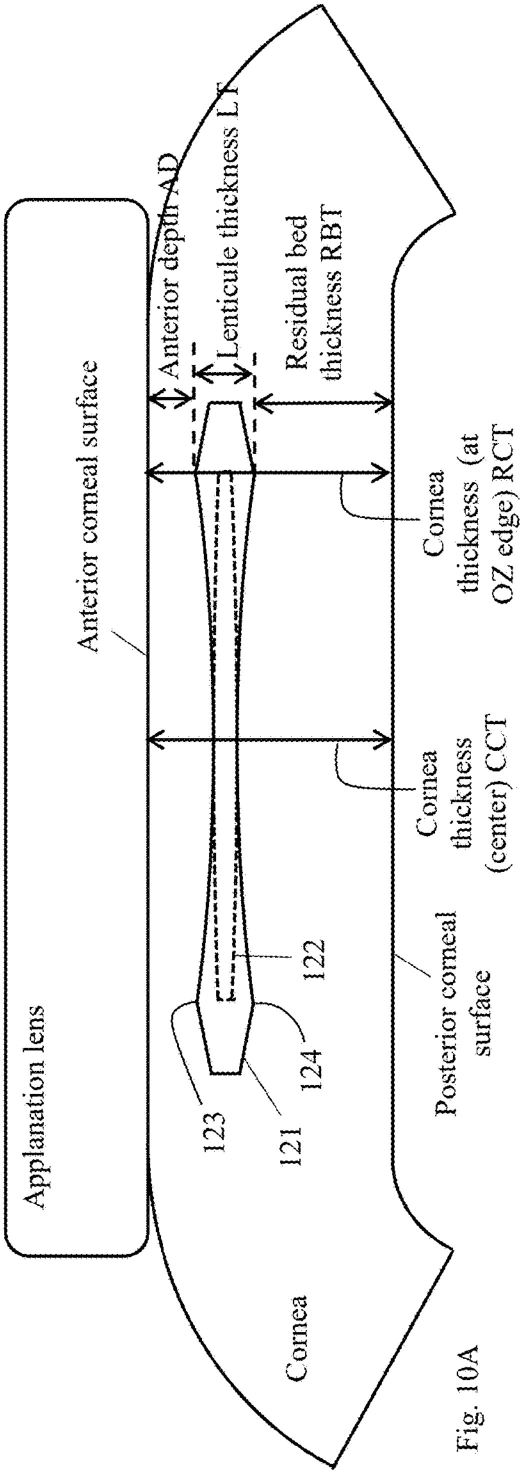
FIGS. 10A-10B schematically illustrate the depth profiles of corneal lenticules for mixed astigmatism correction and hyperopia correction, respectively, according to embodiments of the present invention.

In a fifth embodiment of the present invention, the lenticule incisions are configured by taking into consideration the constraint on residual bed thickness in the periphery region of the lenticule. FIG. 10A (side cross-sectional view) schematically illustrates a lenticule in a cornea that is applanated by an applanation lens. The lenticule in this example is one that treats mixed astigmatism. The solid line outline 121 represents the cross-sectional shape of the lenticule along a first meridian, where the top and bottom incisions have the steepest concave shape among all meridians. The dashed line outline 122 represents the cross-sectional shape of the lenticule along a second meridian perpendicular to the first meridian, where the top and bottom incisions have the steepest convex shape among all meridians. Note that the second meridian is in fact perpendicular to the drawing sheet but the second outline 122 is superimposed on the first outline 121 for comparison purposes. The two cross-sectional shapes 121 and 122 have the same thickness at the lenticule center, but the lenticule becomes thicker toward the periphery along the first meridian, and thinner toward the periphery along the second meridian.

FIG. 10A illustrates the corneal thickness CCT near the corneal center; the corneal thickness RCT in an outer region of the cornea near the optical zone edge of the lenticule; the anterior depth AD of the cornea, which is the depth from the anterior corneal surface to the highest point of the lenticule, in this case the point 123 on the top lenticule incision along the first meridian; the residual bed thickness RBT, which is the distance from the posterior corneal surface to the lowest point of the lenticule, in this case the point 124 on the bottom lenticule incision along the first meridian; and the lenticule thickness LT, which is the vertical distance between the highest point 123 of the top lenticule incision and the lowest point 124 of the bottom lenticule incision. It should be noted that the lenticule thickness LT is not the same concept as the lenticule edge thickness discussed earlier. Also note that although in the example in FIG. 10A, the highest point 123 and the lowest point 124 occur along the same meridian (one of the astigmatism axes), for a more complex lenticule shape, it is possible for the highest and lowest points of the lenticule to be located along two different meridians.

Figure 10B:
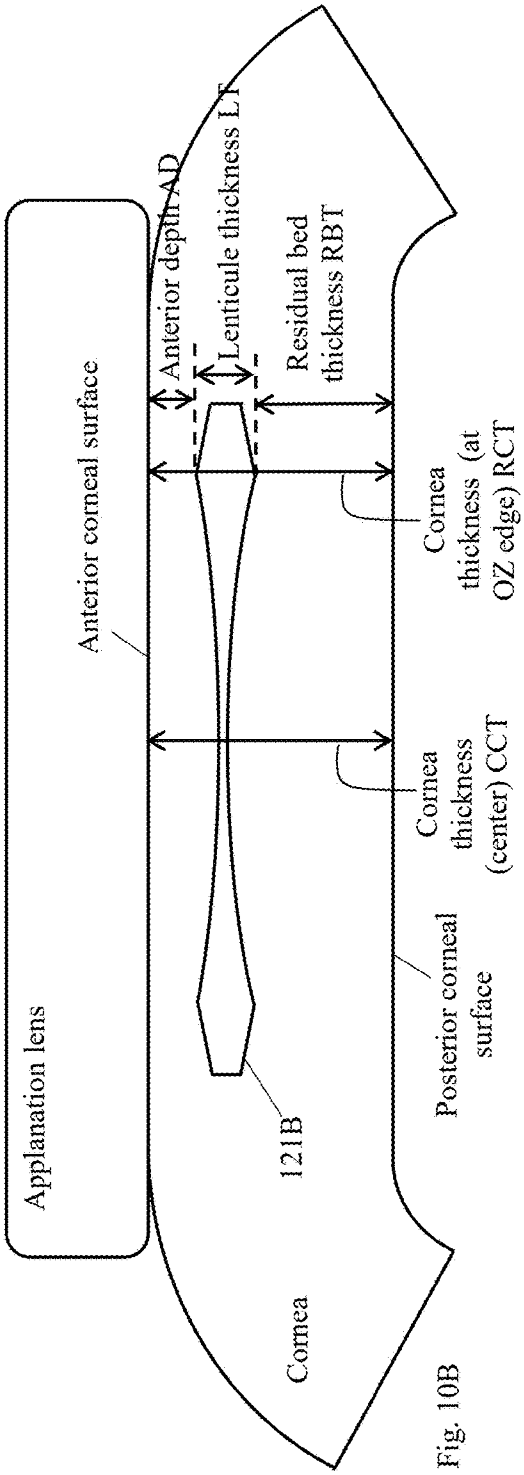

FIG. 10B (side cross-sectional view) is similar to FIG. 10A but illustrates a lenticule for treating hyperopia. In this case, the outline shape of the lenticule along the second meridian is approximately the same as that along the first meridian (121B).

According to the fifth embodiment, the relevant corneal thickness RCT is determined first, for example, based directly or indirectly on measurements by a ranging subsystem of the laser system (e.g., a conventional optical coherence tomography system), and used to calculate the maximum lenticule thickness and maximum attainable refractive power correction. More specifically, the maximum lenticule thickness $LT_{max}$ is calculated by subtracting a minimum acceptable anterior depth $AD_{min}$ and a minimum acceptable residual bed thickness $RBT_{min}$ from the relevant corneal thickness RCT, i.e., $$LT_{max} = RCT - AD_{min} - RBT_{min}$$

The minimum acceptable anterior depth $AD_{min}$, and the minimum acceptable residual bed thickness $RBT_{min}$ are required in order to maintain the mechanical stability of the cornea during and after the lenticule extraction procedure. $AD_{min}$ is preferably about 110 μm, or more generally, from 90 to 150 μm. $RBT_{min}$ is preferably about 250 μm as has been commonly used for LASIK and corneal lenticule procedures, or more generally, from 200 to 300 μm. Note that while the 200 μm value is smaller than the commonly used 250 μm for residual bed thickness, it is adequate because the biomechanics associated with a lenticule procedure is stronger than that resulted from a LASIK procedure. Based on the maximum lenticule thickness $LT_{max}$ determiner above, the maximum refractive power of the lenticule can be calculated. The top and bottom lenticule incisions should be configured such that the lenticule thickness does not exceed the maximum lenticule thickness $LT_{max}$.

For a lenticule for treating myopia, the lenticule is the thickest at the center, and the maximum lenticule thickness is constrained by the center corneal thickness CCT and the minimum acceptable anterior depth and residual bed thickness. As the peripheral corneal thickness PCT is typically greater than the center corneal thickness CCT, e.g., approximately 660 μm at the corneal periphery vs. 550 μm at the corneal center, the relevant corneal thickness RCT used in the above calculation is greater than the center corneal thickness CCT. Because the maximum lenticule thickness $LT_{max}$ is calculated based on the relevant corneal thickness RCT, a larger value can typically be obtained than the maximum lenticule thickness for a lenticule for treating myopia. Thus, larger refractive correction can be obtained compared to lenticules for treating myopia.

The relevant corneal thickness RCT may be directly measured for the individual patient, e.g., using the ranging subsystem of the laser system. Or, the RCT may be calculated from the center corneal thickness CCT and the peripheral corneal thickness PCT as follows, where the CCT and the PCT are either directly measured for the individual patient or known values based on average eyes:

$$RCT = CCT + \frac{OZ^2}{WTW^2}(PCT - CCT)$$

where OZ is the optical zone diameter of the lenticule and WTW is the diameter of the cornea where the peripheral corneal thickness PCT is measured.

All of the lenticule configuration calculation and scan pattern planning described above may be performed by the controller of the laser system based on user input and/or pre-set parameter values for the lenticule. After calculating the shape of the top and bottom lenticules, the controller then controls the laser 14, the energy control system 16, and the scanning system 20 and 28 to direct the pulsed laser beam in the cornea according to the lenticule shape and the scan pattern (e.g. using the fast-scan-slow-sweep scanning scheme) to form the lenticule.

It will be apparent to those skilled in the art that various modification and variations can be made in the corneal lenticule extraction method and related apparatus of the present invention without departing from the spirit or scope of the invention. Thus, it is intended that the present invention cover modifications and variations that come within the scope of the appended claims and their equivalents.

The invention claimed is:

1. A method implemented in an ophthalmic surgical laser system for forming a lenticule in a cornea of a patient's eye to treat hyperopia or mixed astigmatism, the method comprising:

by a laser source, generating a pulsed laser beam comprising a plurality of laser pulses;

by a high frequency scanner, scanning the pulsed laser beam back and forth at a predefined frequency to form a laser beam scanline, the scanline being a straight line having a defined length;

by a scanline rotator, rotating a direction of the scanline around an optical axis of the laser beam;

by a scanning system including an XY-scanner and a Z-scanner, delivering the scanline to the cornea and moving the scanline within the cornea in a depth direction along the optical axis of the laser beam and in two lateral directions perpendicular to the optical axis; and by a controller, controlling the laser source, the high frequency scanner, the scanline rotator, and the scanning system to successively form a first plurality of scanline sweeps which collectively form a first lenticule incision of the lenticule in the cornea, wherein each sweep is formed by placing the scanline perpendicular to a meridian of the first lenticule incision and moving the scanline along the meridian from one edge of the lenticule incision to an opposite edge of the lenticule incision, wherein a sweep angle increment between the meridians of adjacent sweeps is equal to or smaller than a value $\theta_0=\sin^{-1}(L/D)$, wherein L is the length of the scanline and D is a diameter of the lenticule incision.

2. The method of claim 1, wherein the lenticule is configured to treat mixed astigmatism of the eye, and wherein the meridian of one of the sweeps is aligned with an astigmatism axis of the eye.

3. The method of claim 1, further comprising, by the controller, receiving a user input specifying the diameter D of the first lenticule incision, and calculating the value $\theta_0$ based on the diameter D and the scanline length L.

4. The method of claim 1, further comprising, by the controller, controlling the laser source, the high frequency scanner, the scanline rotator, and the scanning system to successively form a second plurality of scanline sweeps which collectively form a second lenticule incision of the lenticule in the cornea, wherein each of the second plurality of scanline sweeps is formed by placing the scanline perpendicular to a meridian of the second lenticule incision and moving the scanline along the meridian from one edge of the second lenticule incision to an opposite edge of the second lenticule incision, wherein a sweep angle increment between the meridians of adjacent sweeps is equal to or smaller than the value $\theta_0$.

5. The method of claim 4, wherein the meridians of the first plurality of sweeps forming the first lenticule incision and the meridians of the second plurality of sweeps forming the second lenticule incision are offset from each other by one half of the sweep angle increment.

6. The method of claim 4, wherein the first lenticule incision is a top lenticule incision and has a concave shape that provides a first refractive power, the second lenticule incision is a bottom lenticule incision and has a concave shape that provides a second refractive power higher than the first refractive power, and wherein a combined refractive power of the top and bottom lenticule incisions is equal to a defined total refractive power.

7. The method of claim 6, further comprising, before forming the top and bottom lenticule incisions:

receiving an input that defines total lower order refractive powers, higher order refractive powers, and a refractive power distribution ratio between the top and bottom lenticule incisions;

calculating lower order refractive powers of the top and bottom lenticule incisions based on the total lower order refractive powers and the refractive power distribution ratio; and adding the higher order refractive powers to the bottom lenticule incision.

8. The method of claim 4, wherein the first lenticule incision is a top lenticule incision and the second lenticule incision is a bottom lenticule incision, the method further comprising forming a ring cut in the cornea, wherein the ring cut extends along an entire periphery of the lenticule and intersect both the top and the bottom lenticule incisions to form an isolated volume of the lenticule, wherein at least one of the top and bottom lenticule incisions is a concave shape along at least one meridian and has different curvatures along two different meridians, and wherein an edge thickness of the lenticule, define as a vertical distance between an intersection of the ring cut with the top lenticule incision and an intersection of the ring cut with the bottom lenticule incision, is a constant value around an entire circumference of the lenticule.

9. The method of claim 8, wherein along at least some meridians, the top lenticule incision curves upwardly and then bends downwardly as it extends toward an edge of the lenticule, and the bottom lenticule incision curves downwardly and then bends upwardly as it extends toward the edge of the lenticule.

10. The method of claim 8, further comprising, before scanning a focus of the laser beam in the cornea:

receiving one or more refractive powers and a lenticule diameter as input from a user;

receiving the constant value of the edge thickness as an input from the user; and calculating shapes of the top and bottom lenticule incisions based at least in part on the one or more refractive powers, the lenticule diameter, and the constant value of the edge thickness.

11. The method of claim 4, wherein the first lenticule incision is a top lenticule incision and the second lenticule incision is a bottom lenticule incision, the method further comprising, before forming the top and bottom lenticule incisions:

calculating a shape of the top lenticule incision based on a refractive power and a diameter of the top lenticule incision, the shape being a concave shape along at least some meridians, with a highest point located near a periphery of the top lenticule incision;

calculating a depth of the top lenticule incision within the cornea by placing the highest point at a predefined depth below an anterior corneal surface; and calculating a shape and a depth of the bottom lenticule incision based on a refractive power and a diameter of the bottom lenticule incision;

wherein the top lenticule incision and the bottom lenticule incision are formed according to the calculated shapes and depths.

12. The method of claim 11, further comprising, before calculating a depth of the top lenticule incision, receiving the predefined depth as an input from a user.

13. The method of claim 4, wherein the first lenticule incision is a top lenticule incision and the second lenticule incision is a bottom lenticule incision, the method further comprising, before forming the top and bottom lenticule incisions:

determining a corneal thickness in an outer area of the cornea near an edge of the lenticule;

calculating a maximum lenticule thickness by subtracting a minimum anterior depth and a minimum residual bed thickness from the corneal thickness; and calculating shapes of a top lenticule incision and a bottom lenticule incision, wherein along at least one meridian, both the top lenticule incision and the bottom lenticule incision have a concave shape, and wherein a vertical distance between a highest point of the top lenticule incision and a lowest point of the bottom lenticule incision is smaller than or equal to the maximum lenticule thickness;

wherein the top lenticule incision and the bottom lenticule incision are formed according to the calculated shapes.

14. The method of claim 13, wherein the minimum anterior depth is from 90 to 150 μm and the minimum residual bed thickness is from 200 to 300 μm.

15. An ophthalmic surgical laser system for forming a lenticule in a cornea of a patient's eye to treat hyperopia or mixed astigmatism, comprising:

a laser source configured to generate a pulsed laser beam comprising a plurality of laser pulses;

a high frequency scanner configured to scan the pulsed laser beam back and forth at a predefined frequency to form a laser beam scanline, the scanline being a straight line having a defined length;

a scanline rotator configured to rotate a direction of the scanline around an optical axis of the laser beam;

a scanning system including an XY-scanner and a Z-scanner, configured to deliver the scanline to the cornea and move the scanline within the cornea in a depth direction along the optical axis of the laser beam and in two lateral directions perpendicular to the optical axis; and a controller configured to control the laser source, the high frequency scanner, the scanline rotator, and the scanning system to successively form a first plurality of scanline sweeps which collectively form a first lenticule incision of the lenticule in the cornea, including forming each sweep by placing the scanline perpendicular to a meridian of the first lenticule incision and moving the scanline along the meridian from one edge of the lenticule incision to an opposite edge of the lenticule incision, wherein a sweep angle increment between the meridians of adjacent sweeps is equal to or smaller than a value $\theta_0=\sin^{-1}(L/D)$, wherein L is the length of the scanline and D is a diameter of the lenticule incision.

16. The system of claim 15, wherein the controller is further configured to receive a user input specifying the diameter D of the first lenticule incision, and to calculate the value $\theta_0$ based on the diameter D and the scanline length L.

17. The system of claim 15, wherein the controller is further configured to control the laser source, the high frequency scanner, the scanline rotator, and the scanning system to successively form a second plurality of scanline sweeps which collectively form a second lenticule incision of the lenticule in the cornea, including forming each of the second plurality of scanline sweeps by placing the scanline perpendicular to a meridian of the second lenticule incision and moving the scanline along the meridian from one edge of the second lenticule incision to an opposite edge of the second lenticule incision, wherein a sweep angle increment between the meridians of adjacent sweeps is equal to or smaller than the value $\theta_0$.

18. The system of claim 17, wherein the meridians of the first plurality of sweeps forming the first lenticule incision and the meridians of the second plurality of sweeps forming the second lenticule incision are offset from each other by one half of the sweep angle increment.

19. The system of claim 15, wherein the lenticule is configured to treat mixed astigmatism of the eye, and wherein the meridian of one of the sweeps is aligned with an astigmatism axis of the eye.

20. A method implemented in an ophthalmic surgical laser system for forming a lenticule in a cornea of a patient's eye to treat hyperopia or mixed astigmatism, the method comprising:

operating the ophthalmic surgical laser system to generate a pulsed laser beam; and scanning a focus of the laser beam in the cornea to form a top lenticule incision, a bottom lenticule incision, and a ring cut in the cornea, wherein the ring cut extends along an entire periphery of the lenticule and intersect both the top and the bottom lenticule incisions to form an isolated volume of the lenticule, wherein at least one of the top and bottom lenticule incisions is a concave shape along at least one meridian and has different curvatures along two different meridians, and wherein an edge thickness of the lenticule, define as a vertical distance between an intersection of the ring cut with the top lenticule incision and an intersection of the ring cut with the bottom lenticule incision, is a constant value around an entire circumference of the lenticule.

* * * * *